US00PP32639P2

(12) United States Plant Patent
Beekenkamp

(10) Patent No.: US PP32,639 P2
(45) Date of Patent: Dec. 15, 2020

(54) ***BEGONIA* PLANT NAMED 'BKPBEESM'**

(50) Latin Name: ***Begonia* x *hiemalis***
Varietal Denomination: BKPBEESM

(71) Applicant: Annie Cornelia Beekenkamp, Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 16/873,392

(22) Filed: Apr. 4, 2020

(51) Int. Cl.
*A01H 5/02* (2018.01)
*A01H 6/18* (2018.01)

(52) U.S. Cl.
USPC ..... Plt./347

(58) Field of Classification Search
USPC ..... Plt./347, 346, 344, 348
CPC ... A01H 5/02; A01H 5/00; A01H 6/18; A01H 6/185
See application file for complete search history.

*Primary Examiner* — June Hwu
(74) *Attorney, Agent, or Firm* — C. Anne Whealy

(57) ABSTRACT

A new and distinct cultivar of *Begonia* plant named 'BKPBEESM', characterized by its broadly upright and mounded plant habit; sturdy plants with freely basal branching habit; dark green-colored leaves; uniform and freely flowering habit; and double flowers that are yellowish orange to yellowish pink in color with light red-colored margins.

2 Drawing Sheets

Figure 1:
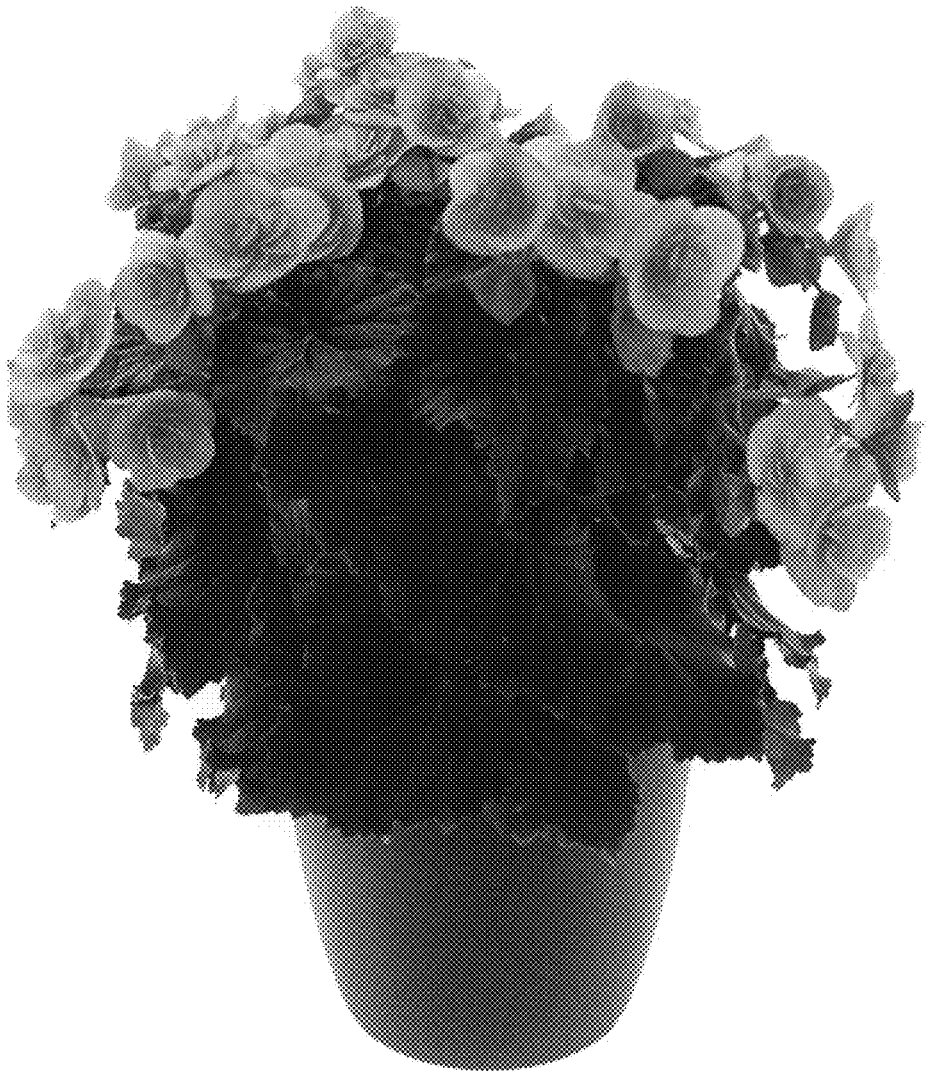

Botanical designation: *Begonia* x *hiemalis*.
Cultivar denomination: 'BKPBEESM'.

BACKGROUND OF THE INVENTION

The present invention relates to a new and distinct cultivar of *Begonia* plant, botanically known as *Begonia* x *hiemalis*, commercially referred to as Elatior Begonia and hereinafter referred to by the name 'BKPBEESM'.

The new *Begonia* plant is a product of a planned breeding program conducted by the Inventor in Maasdijk, The Netherlands. The objective of the breeding program was to develop new freely branching and freely flowering *Begonia* plants with attractive flowers and good garden performance.

The new *Begonia* plant originated from a cross-pollination made by the Inventor in September, 2009 of a proprietary selection of *Begonia* x *tuberhybrida* identified as code number 07-077-01, not patented, as the female, or seed, parent with an unnamed proprietary selection of *Begonia socotrana*, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in February, 2010.

Asexual reproduction of the new *Begonia* plant by vegetative tip cuttings in a controlled greenhouse environment in Maasdijk, The Netherlands since July, 2010 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEESM'. These characteristics in combination distinguish 'BKPBEESM' as a new and distinct *Begonia* plant:

1. Broadly upright and mounded plant habit.
2. Sturdy plants with freely basal branching habit.
3. Dark green-colored leaves.
4. Uniform and freely flowering habit.
5. Double flowers that are yellowish orange to yellowish pink in color with light red-colored margins.

Plants of the new *Begonia* can be compared to plants of the female parent selection. Plants of the new *Begonia* differ primarily from plants of the female parent selection in the following characteristics:

1. Plants of the new *Begonia* have smaller flowers than plants of the female parent selection.
2. Plants of the new *Begonia* have yellowish orange to yellowish pink-colored flowers with light red-colored margins whereas plants of the female parent selection have yellow-colored flowers.

Plants of the new *Begonia* can be compared to plants of the male parent selection. Plants of the new *Begonia* differ primarily from plants of the male parent selection in the following characteristics:

1. Plants of the new *Begonia* have double-type flowers whereas plants of the male parent selection have single-type flowers.
2. Plants of the new *Begonia* have yellowish orange to yellowish pink-colored flowers with light red-colored margins whereas plants of the male parent selection have pink-colored flowers.

Plants of the new *Begonia* can be compared to plants of *Begonia* x *hiemalis* 'Bkpbeeas', disclosed in U.S. Plant Pat.

No. 29,247. Plants of the new *Begonia* differ primarily from plants of 'Bkpbeeas' in the following characteristics:

1. Plants of the new *Begonia* have smaller flowers than plants of 'Bkpbeeas'.
2. Plants of the new *Begonia* have yellowish orange to yellowish pink-colored flowers with light red-colored margins whereas plants of 'Bkpbeeas' have orange red-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical flowering plant of 'BKPBEESM' grown in a container.

Figure 2:
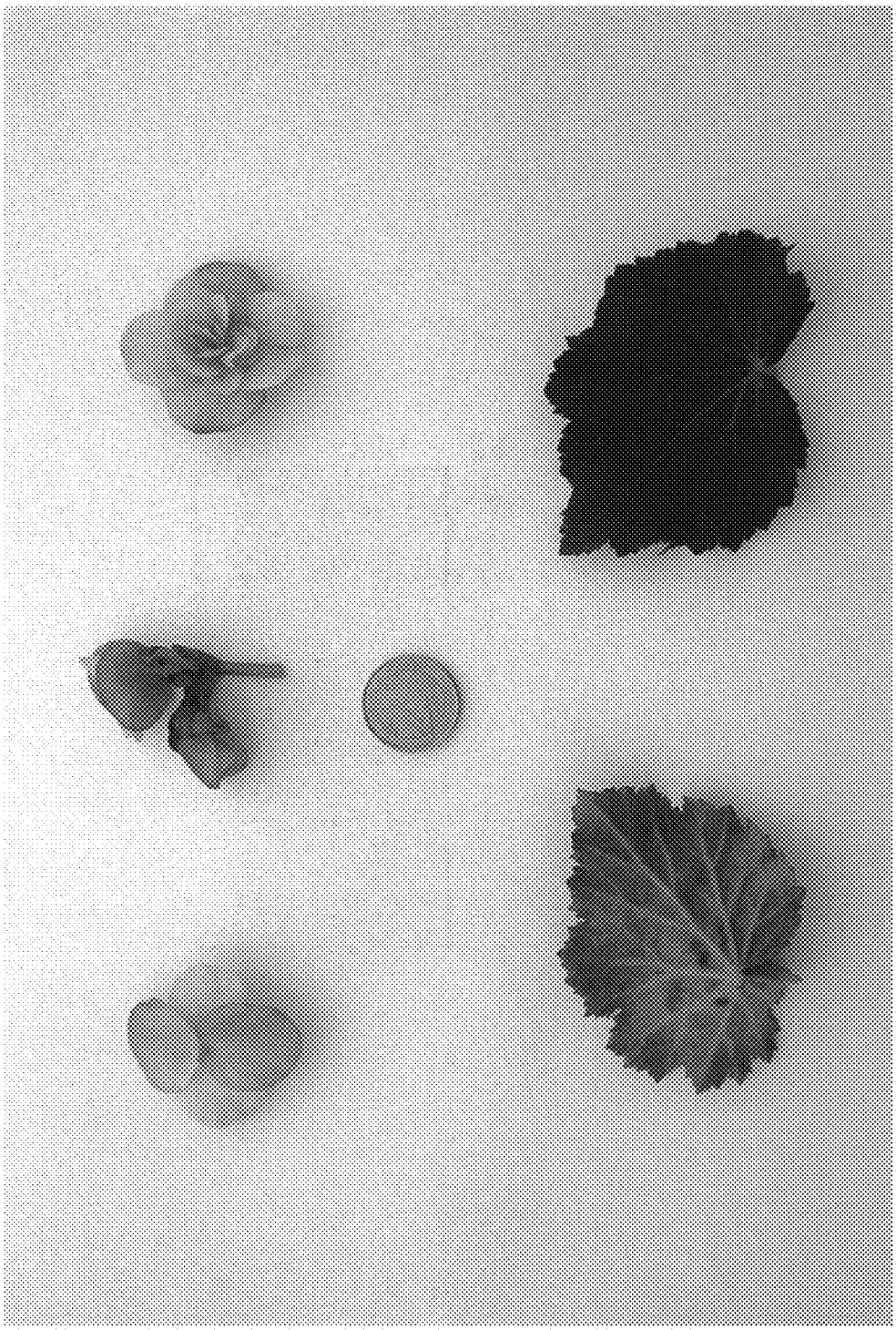

The photograph on the second sheet (FIG. 2 of 2) are close-up views of a typical flower bud and the upper and lower surfaces of typical developed flowers and leaves of 'BKPBEESM'.

DETAILED BOTANICAL DESCRIPTION

Plants used for the aforementioned photographs and following observations and measurements were grown during the summer in 10.5-cm containers in a glass-covered greenhouse in Dinslaken, Germany. During the production of the plants, day and night temperatures ranged from 19° to 21° C. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'BKPBEESM'.

Parentage:

*Female, or seed, parent.*—Proprietary selection of *Begonia* x *tuberhybrida* identified as code number 07-077-01, not patented.

*Male, or pollen, parent.*—Unnamed proprietary selection of *Begonia socotrana*, not patented.

Propagation:

*Type.*—By vegetative tip cuttings.

*Time to initiate roots.*—About 20 days at temperatures about 25° C.

*Time to produce a rooted young plant.*—About 35 to 36 days at temperatures about 21° C. to 23° C.

*Root description.*—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit.*—Freely branching habit; dense.

Plant description:

*Plant and growth habit.*—Broadly upright and mounded plant habit; overall plant shape, globular; moderately vigorous growth habit and moderate growth rate.

*Plant height, soil level to top of foliar plane.*—About 21.7 cm.

*Plant height, soil level to top of floral plane.*—About 24.7 cm.

*Plant width.*—About 32.5 cm.

*Lateral branch description.*—Branching habit: Freely branching habit with about six basal branches developing per plant; pinching is not required. Length: About 13.3 cm. Diameter: About 9 mm. Internode length: About 2.5 cm. Strength: Moderately strong. Aspect: About 27.5° from vertical. Texture and luster: Sparsely pubescent; slightly glossy. Color, developing: Close to 144A. Color, fully developed: Close to 146C; proximally, tinged with close to 181A.

*Leaf description.*—Arrangement: Alternate, simple. Length: About 11 cm. Width: About 8.4 cm. Shape: Broadly ovate. Apex: Acute. Base: Oblique, lobes not imbricate. Margin: Dentate to crenate; moderately to strongly undulate. Texture and luster, upper and lower surfaces: Smooth, glabrous; velvety; slightly glossy. Venation pattern: Palmate. Color: Developing leaves, upper surface: Close to between NN137A and 147A. Developing leaves, lower surface: Close to N148A. Fully expanded leaves, upper surface: Slightly darker than between NN137A and 147A; venation, close to 143B and proximally, close to 183D. Fully expanded leaves, lower surface: Close to between 194A and 197B; venation, close to 146C. Petioles: Length: About 5.3 cm. Diameter: About 4.5 mm. Strength: Moderately strong, flexible. Texture and luster, upper and lower surfaces: Sparsely pubescent; slightly glossy. Color, upper surface: Close to 152A; proximally, close to 152B; distally, close to 185A. Color, lower surface: Close to 152B; distally tinged with close to 185B. Stipules: Quantity per leaf: Two. Length: About 9 mm. Width: About 9 mm. Shape: Broadly ovate to deltoid. Apex: Bluntly acute, ciliate. Base: Broadly cuneate. Margins: Entire, ciliate. Color, upper and lower surfaces: Close to 146C and 146D; towards the margins and apex, close to 157D.

Flower description:

*Flowering habit.*—Rotate double sterile flowers arranged in axillary compound cymes; freely flowering habit with about five flowers per cyme and about 175 flowers developing per plant during the flowering season; flowers face upright to outwardly.

*Fragrance.*—None detected.

*Natural flowering season.*—Long flowering period, plants flower freely and continuously from spring into the autumn in The Netherlands; during the winter in a greenhouse, plants begin flowering about five weeks after exposure to photoinductive treatments.

*Postproduction longevity.*—Individual flowers last about ten days on the plant; flowers not persistent; plants maintain good substance for about 20 to 30 days in an interior environment.

*Inflorescence height.*—About 9.5 cm.

*Inflorescence diameter.*—About 8.8 cm.

*Flower buds.*—Length: About 1.6 cm. Diameter, flattened: About 7 mm to 14 mm. Shape: Broadly obovate to inverted deltoid; flattened. Texture and luster: Smooth, glabrous; velvety; matte. Color: Close to 39A.

*Flowers.*—Diameter: About 4.5 cm. Depth: About 1.9 cm. Tepals: Quantity and arrangement: Four per flower arranged in two whorls. Length, lower tepals: About 2.5 cm. Width, lower tepals: About 2.7 cm. Length, upper tepals: About 2.3 cm. Width, upper tepals: About 2.3 cm. Shape, lower tepals: Roughly reniform. Shape, upper tepals: Broadly obovate. Apex, lower and upper tepals: Rounded. Base, lower tepals: Broadly cuneate. Base, upper tepals: Cuneate. Margin, lower and upper tepals: Entire; not undulate to slightly undulate. Texture and luster, lower and upper tepals, upper surface: Smooth, glabrous, velvety; matte. Texture and luster, lower and upper tepals, lower surface: Smooth, glabrous, velvety; matte and at the base, slightly glossy. Color, lower tepals: When opening, upper surface: Close to 23C; towards the apex and margins, close to 37A; at the margins, close to 41A; towards the base, close to 26A to 26B. When opening, lower surface: Close to 37A; at the margins, close to 43A to 43B; towards the base, tinged with close to 154D. Fully opened, upper surface: Close to 37C; at the margins, close to 39A; towards the base, tinged with close to 1B; venation, close to 35C; color does not fade with development. Fully opened, lower surface: Close to 39B; towards the apex and margins, close to 39C; at the margins, close to 41B; venation, close to 161A; color does not fade with development. Color, upper tepals: When opening, upper surface: Close to 16B; towards the apex, close to 26C; towards the base, tinged with close to 19A. When opening, lower surface: Close to 26D ringed with close to 35C. Fully opened, upper surface: Close to between 19A and 20A; at the apex and margins, close to 36C to 36D; venation, close to 35C; color does not fade with development. Fully opened, lower surface: Close to 38C to 38D tinged with close to 27B; venation, close to 161A; color does not fade with development.

*Tepaloids.*—Quantity and arrangement: About 20 arranged in about four whorls at the center of the flower. Length: About 1.4 cm. Width: About 1 cm. Shape: Obovate to broadly obovate. Apex: Obtuse to broadly and bluntly acute. Base: Cuneate. Margin: Entire; not undulate. Texture and luster, upper and lower surfaces: Smooth, glabrous, velvety; matte. Color: When opening, upper surface: Close to 21D; margins, close to 31C. When opening, lower surface: Close to 29C; margins, close to 41C to 41D. Fully opened, upper surface: Close to 12A to 12B; towards the apex, close to 39C; venation, similar to lamina colors; color does not change with development. Fully opened, lower surface: Close to 38D; towards the base, tinged with close to 4D; at the margins, close to 39B; venation, similar to lamina colors; color does not change with development.

*Peduncles.*—Length: About 4.3 cm. Diameter: About 4 mm. Angle: About 30° from lateral branch axis. Strength: Moderately strong; flexible. Texture and luster: Smooth, glabrous; moderately glossy. Color: Close to 144A.

*Pedicels.*—Length: About 2 cm. Diameter: About 2 mm. Angle: About 30° from the peduncle axis. Strength: Moderately strong; flexible. Texture and luster: Moderately pubescent; moderately glossy. Color: Close to 173A to 173B; proximally, close to 146D.

*Flower bracts.*—Quantity and arrangement: Two per flower, opposite. Length: About 1.2 cm. Width: About 1.4 cm. Shape: Reniform. Apex: Obtuse; ciliate. Base: Broadly cuneate. Margin: Entire; ciliate. Texture and luster, upper and lower surfaces: Smooth, glabrous; slightly glossy. Color, upper surface: Close to 144A to 144B; at the margins, close to 179B. Color, lower surface: Close to 175B.

*Reproductive organs.*—None observed, all structures transformed into tepaloids.

*Seeds and fruits.*—Seed and fruit development have not been observed on plants of the new *Begonia* as flowers are sterile.

Pathogen & pest resistance: Resistance to pathogens and pests common to *Begonia* plants has not been observed on plants of the new *Begonia.*

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBEESM' as illustrated and described.

* * * * *